United States Patent [19]

Sakata et al.

[11] Patent Number: 4,740,460
[45] Date of Patent: Apr. 26, 1988

[54] PROCESS FOR MEASURING ENDOTOXIN AND APPARATUS USED THEREFOR

[75] Inventors: Yoshitsugu Sakata, Ootsu; Haruki Oishi, Ikeda; Yasumichi Hatayama, Osaka; Hiromi Shiraishi, Toyonaka; Kazuya Yanagisawa, Itami, all of Japan

[73] Assignee: Wako Pure Chemical Industries, Ltd., Osaka, Japan

[21] Appl. No.: 748,805

[22] Filed: Jun. 26, 1985

[30] Foreign Application Priority Data

Jun. 27, 1984 [JP] Japan .................. 59-132445
Dec. 28, 1984 [JP] Japan .................. 59-281616

[51] Int. Cl.$^4$ .................... G01N 33/579
[52] U.S. Cl. .................... 435/18; 73/64.1; 422/73; 436/502; 436/517; 436/805
[58] Field of Search ............ 436/502, 517, 805; 422/73; 73/64.1; 435/18

[56] References Cited

U.S. PATENT DOCUMENTS

| | | | |
|---|---|---|---|
| 3,458,287 | 7/1969 | Gross | 23/230 |
| 4,038,029 | 7/1977 | Teller | 436/502 |
| 4,205,954 | 6/1980 | Babson | 436/517 |
| 4,224,304 | 9/1980 | Sawai | 436/517 |
| 4,268,171 | 5/1981 | Sternberg | 436/517 |
| 4,454,752 | 6/1984 | Scoraato | 73/64.1 |
| 4,492,462 | 1/1985 | Pross | 73/64.1 X |

FOREIGN PATENT DOCUMENTS 0010526 4/1980 European Pat. Off. .
0061431 9/1982 European Pat. Off. .
WOA83/002-
28 1/1983 Fed. Rep. of Germany .

OTHER PUBLICATIONS

Search Report from EP 85 10 7877.4.
2200 Medical & Biological Engineering & Computing 22 (1984) Sep., No. 5, Staines, Middlesex, Great Britain, pp. 401–405.
J. Lab. Clin. Med., vol. 75, No. 6, Jun. 1970, pp. 903–911, US; J. Levin et al.: "Detection of Endotoxin in Human Blood and Demonstration of an Inhibitor".

Primary Examiner—Sidney Marantz
Attorney, Agent, or Firm—Armstrong, Nikaido, Marmelstein & Kubovcik

[57] ABSTRACT

Endotoxin contents in samples can be determined qualitatively, or quantitatively, singly or in parallel, with high precision in a short time by a process comprising applying a light to each sample solution, measuring an initial transmitted light amount $I_0$ and a transmitted light amount at a time t, $I(t)$, to give a ratio $R(t)=I(t)/I_0$, and judging a gelation point by a threshold value of $R(t)$, or further obtaining a gelation time from the gelation point. An apparatus used therefor is also disclosed.

21 Claims, 6 Drawing Sheets

PROCESS FOR MEASURING ENDOTOXIN AND APPARATUS USED THEREFOR

BACKGROUND OF THE INVENTION

This invention relates to a process for measuring an endotoxin in a sample and an apparatus used therefor.

Endotoxins are a typical fever-producing substance (pyrogen). When a blood, transfusion solution or parenteral solution contaminated by an endotoxin is inserted into a living body, it is known to produce serious side effects such as a high fever or shock. Therefore, it is absolutely necessary to measure the amount of exdotoxin in a raw material solution, washing water, etc., in order to prevent the contamination with the endotoxin in the production steps of medical products such as injections. Further, the measurement of endotoxin is widely applied, for example, to a functional test for ultrapure water producing membranes, or to an examination of washing water used in the production of semiconductors.

Recently, there has been developed a method for measuring an endotoxin by applying a gelation reaction between the Limulus amoebocyte lysate (a component extracted from amoebocytes of Limulus polyphemus, hereinafter referred to as "LAL") and an endotoxin [J. Levin & F. B. Bang, Thromb. Diath. Haemorrh., 19, 186 (1968)]. This method comprises mixing a sample solution and an LAL reagent in a test tube, allowing to stand at a constant temperature for a certain period of time, observing with the naked eye the formation of gel by declining or inverting the test tube, comparing with the results of similar reaction between an endotoxin-containing sample with known concentration and the LAL reagent, and judging semiquantitatively whether the sample solution is endotoxin-positive (+) or negative (−). But since this method requires much skill and the judging standard of positive or negative depends on observer's subjectivity, there are various disadvantages in that the judgement reflects greatly personal differences, the lower limit of judgement is about 0.05 ng/ml and a further lower concentration of endotoxin cannot be detected, and the like. In addition, the strength of gel state in the gelation reaction is so weak that the gel state is easily broken sometimes by a slight swing of the test tube by a water stream in a water recycling type constant temperature bath which is used for maintaining the reaction at a constant temperature such as at 37° C., or by a slight move of the test tube when it is taken out of the constant temperature bath for the observation by the naked eye, which results in producing an error. Therefore, it is very difficult to obtain precise measured values stably by this method.

Recently, there is proposed a method for determining the endotoxin content by measuring optically the turbidity of samples and using the changes of absorbances, noticing that the turbidity is produced by the gelation (e.g. Japanese patent unexamined publication Nos. 9050/83 and 42451/84). According to this method, objectivity of the judgement is improved, but since it requires several tens minutes to about 1 hour for the gelation reaction, a longer time is necessary for measuring a plurality of samples and the measuring efficiency is remarkably bad. Further, when a sample moving system is employed in an absorbance measuring apparatus for measuring a large number of samples continuously in order to improve the efficiency, there is a danger of breaking the gel state of samples in the course of gelation due to the weakness of gel as mentioned above. Therefore, it is difficult to say that this method is a practical one for measuring a plurality of samples in a short time.

On the other hand, there is developed a method for determining an endotoxin content by using a chromogenic peptide derivative as a synthetic substrate, conducting a color development by hydrolysis of the substrate with LAL and endotoxin in a sample, and colorimetrically determining the degree of coloring [S. Iwanaga et al., Haemostasis, 7, 183 (1978)]. But this method is not suitable for daily examinations since the measurable range is as narrow as from several pg/ml to 100 pg/ml and the measuring procedures are remarkably complicated.

SUMMARY OF THE INVENTION

It is an object of this invention to provide a process for measuring an endotoxin in a sample in a remarkably wide range of concentrations with a high precision with ease even if a large number of samples are used, overcoming the disadvantages of the prior art methods. It is another object of this invention to provide an apparatus usable for such a process.

This invention provides a process for measuring an endotoxin which comprises mixing a sample with an endotoxin gelating reagent to give one or more sample solutions, applying a light to each sample solution, measuring a transmitted light amount at an initial stage $I_0$ and that after a reaction time t, $I(t)$, in each sample solution to give a ratio $R(t)=I(t)/I_0$, and judging a gelation point by the ratio $R(t)$ reaching a certain value in the range of 75 to 97%.

This invention also provides a process for measuring an endotoxin which comprises mixing a sample with an endotoxin gelating reagent to give one or more sample solutions, applying a light to each sample solution, measuring a transmitted light amount at an initial stage $I_0$ and that after a reaction time t, $I(t)$, in each sample solution to give a ratio $R(t)=I(t)/I_0$, judging a gelation point by the ratio $R(t)$ reaching a certain value in the range of 75 to 97%, obtaining a gelation time $T_G$ from a time required for reaching the gelation point from the mixing of the sample and the endotoxin gelating reagent, and determining the endotoxin content in the sample based on a relation between the standard endotoxin contents and the gelation times previously obtained.

This invention further provides an apparatus for measuring an endotoxin comprising one or more optical systems each comprising a light source, a sample solution-holding vessel, and a means for detecting transmitted light amounts, a constant temperature bath for maintaining the optical systems at a constant temperature and keeping the vessel still, a means for correcting the sensitivity of the optical systems and for judging a gelation point, a means for instructing the initiation of measurement of transmitted light amounts connected to the means for correction and judgement, and a timer for measuring the time passed from the initiation of measurement of transmitted light amounts for each optical system in parallel and independently and connected to the means for correction and judgement.

DESCRIPTION OF THE PREFERRED EMBODIMENTS

Figure 1:
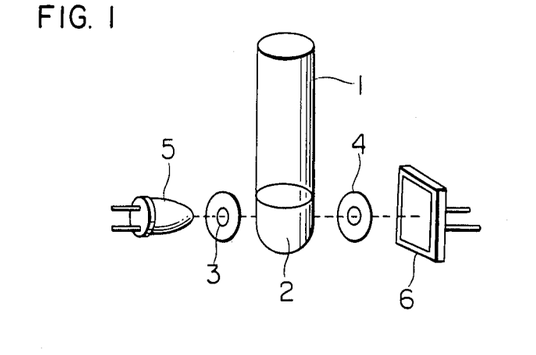
FIG. 1 is a perspective view showing an optical system comprising a light source, a sample solution-holding vessel, and a means for detecting transmitted light amounts.

In this invention, an optical system as shown in FIG. 1, for example, can be used for measuring transmitted light amounts of sample solutions. That is, a sample solution-holding vessel, for example a cuvette 1 (usually having an inner diameter of 6 mm to 12 mm) contains a sample solution 2 obtained by mixing a liquid sample to be examined and an endotoxin gelating reagent such as LAL reagent (usually 0.1 ml of the liquid sample and 0.1 ml of the LAL reagent, or freeze-dried LAL reagent and 0.2 ml of the liquid sample). A light from a light source 5 is applied through an aperture 3 to the sample solution 2. The light transmitted through the sample solution 2 passes through an aperture 4 and is converted to the corresponding quantity of electricity at a means for detecting transmitted light amounts such as a photoelectric detector 6.

As the light source 5, there can be used a light-emitting element such as a light-emitting diode (LED), a tungsten lamp, or the like.

As the photoelectric detector 6, there can be used a light-receiving element such as a photodiode, a photocell, or the like.

Figure 2:
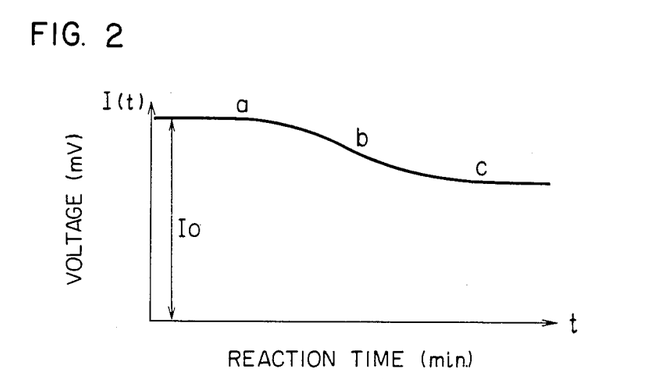
FIG. 2 is a graph showing a change of transmitted light amount I(t) of a sample solution with the lapse of time.

The transmitted light amount I(t) detected by the photoelectric detector 6 shows a change with the lapse of time against the reaction time "t" after the mixture of the liquid sample and the LAL reagent as shown in FIG. 2. That is, the gelation of endotoxin takes place after three steps, that is, a step (a) wherein the transmitted light shows an initial value $I_0$ with an almost constant value at the initial stage of the reaction, a step (b) wherein the transmitted light I(t) decreases rapidly, and finally a step (c) wherein I(t) shows an almost constant value with almost no changes. As is clear from FIG. 2, the step (b) shows a state of rapidly progressing the gelation in the sample solution, and the step (c) shows a state to be judged positive in the gelation reaction according to the prior art gel-clotting method by the naked eye. Since the time necessary to reach the stage (b) and the stage (c) from the beginning of the reaction has a relation to the exdotoxin concentration in sample solutions and this is confirmed experimentally, it becomes possible to measure the endotoxin qualitatively and quantitatively in a wide range with excellent precision by applying such a relation. Further such a method can easily be applied to daily examinations.

It is important in this invention that the sensitivity of individual optical systems is corrected properly. In addition, in order to correct differences in transmitted light amounts derived from clouding and coloring inherent to sample solutions, the initial value of transmitted light amount $I_0$ and the transmitted light amount at a time "t" from the beginning of the reaction I(t) are measured and the ratio R(t), that is, $$R(t) = I(t)/I_0 \times 100 \ (\%)$$

is obtained. That is, R(t) is corrected in differences in sensitivity of the optical systems and in differences in light amounts depending on the state of samples.

Figure 3:
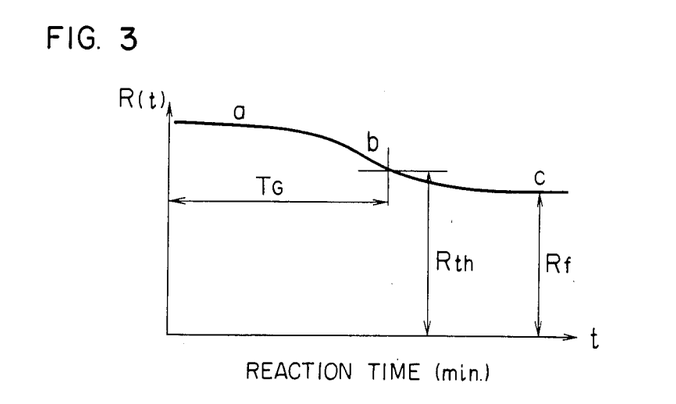
FIG. 3 is a graph showing a change of the ratio R(t) with the lapse of time.

The change of R(t) with the lapse of time is as shown in FIG. 3, which shows the same behavior as the change of I(t) as shown in FIG. 2.

As the initial value $I_0$, it is possible to employ four values, a maximum initial value $I_{0.max}$, an average initial value $I_{0.av}$, an initial value at a special point of time "ts" $I_{0.ts}$, and a minimum initial value $I_{0.min}$, measured in a period from the mixing of the liquid sample with the endotoxin gelating reagent to the lowering in transmitted light amount due to the beginning of the reaction—about 2 minutes.

The maximum initial value $I_{0.max}$ is employed when it takes a longer time for making the mixed solution of the reagent and the sample uniform, particularly in the case of using a freeze-dried reagent, or bubbles are included at the mixing time of the reagent and the sample.

The average initial value $I_{0.av}$ is employed when fast alternating current noise is added to a signal due to the presence of fine microparticles, or there is slow alternating current noise due to moving of relatively large particles.

The minimum initial value $I_{0.min}$ is employed when it takes a longer time to make the mixture of the reagent and the sample uniform.

The initial value at a special point of time "ts", $I_{0.ts}$, is employed when a time zone is previously known for obtaining correct value of $I_0$ in the case of measuring the maximum value or minimum value.

Considering properties of the reagent, the use of the initial value $I_{0.max}$ is preferable.

In this invention, a constant R(t) value, i.e. Rf, at which I(t) is hardly changed and shows a constant value in the stage (c), is not used since it takes a long time to obtain the Rf value. Instead, a threshold value $R_{th}$ at the stage (b) wherein the gelation reaction proceeds is provided as shown in FIG. 3 and the point of time arrived at the threshold value $R_{th}$ is judged as "a gelation point". Further, the reaction time from the mixing of the sample solution to the gelation point is defined as "a gelation time $T_G$", which is used for the quantitative determination of endotoxins.

The threshold value $R_{th}$ can be provided optionally considering that no error is produced by noise and all the samples are fallen in the provided value. Further since the gelation time $T_G$ is determined by $R_{th}$ which is not dependent on the optical systems and can be set as a common value, $T_G$ is also not dependent on properties of each optical system. When a relation between the gelation time and the endotoxin is known, the endotoxin concentration can be obtained by measuring the gelation time.

Figure 4:
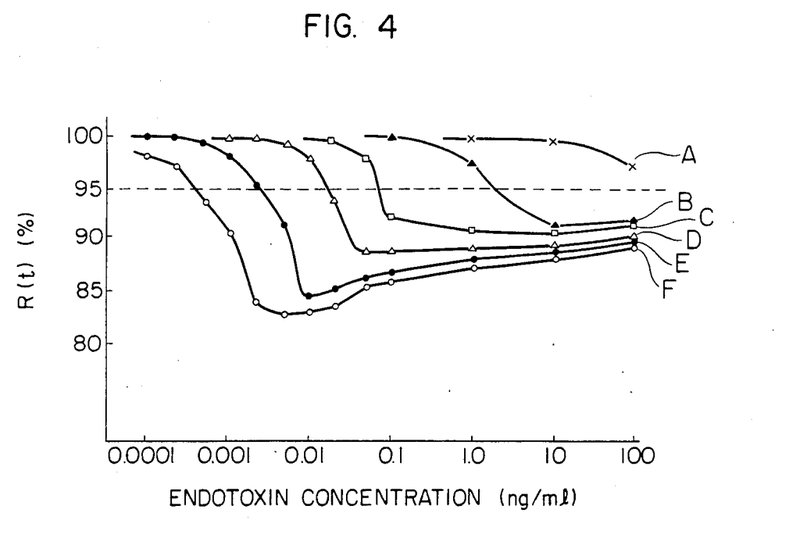
FIG. 4 is a graph showing changes of the ratio R(t) with the lapse of time against endotoxin concentrations.

FIG. 4 is a graph obtained by plotting the relation of endotoxin concentration and R(t) using a passed time from the mixing of sample solution as a parameter. The reagent used and measuring method are as follows.

LAL reagent: manufactured by Associates of Cape Cod. The sensitivity of the gel-clotting method by means of FDA reference 0.05 ng/ml.

Endotoxin: purified from *Escherichia coli* UKT-B (Research Institute for Microbial Diseases, Osaka University).

The content is determined by FDA reference.

Measuring method: The LAL reagent and the endotoxin are dissolved in distilled water for injection (manufactured by Otsuka Pharmaceutical Co., Ltd.) respectively, and mixed in a test tube having a diameter of 10 mm in amounts of each 0.1 ml with stirring, and changes of transmitted light amounts are measured while maintaining the sample solutions at 37° C.

In FIG. 4, curves A, B, C, D, E and F show the changes after 5, 10, 20, 35, 60 and 120 minutes from the mixing, respectively.

As is clear from FIG. 4, R(t) is lowered in all the concentrations measured, and the higher the concentration of sample solutions, the faster the beginning of the lowering. Further, the final value Rf at which R(t) shows almost no lowering with the lapse of time, does not show a remarkable difference corresponding to concentration changes, and thus Rf is not suitable as indicator of endotoxin concentration. In contrast, when $R_{th}$ value which is a value before R(t) reaches Rf is used ($R_{th}$ is shown by a dashed line in FIG. 4 at R(t)=95%), gelation of sample solutions can be judged in a wider range of the concentration. Further, by measuring the reaction time until R(t) reaches $R_{th}$ as the gelation time $T_G$, the quantitative determination of endotoxin concentration can be carried out in a wide range. The time required for R(t) reaching Rf changes depending on the sensitivity of LAL reagent, the shape of cuvettes, and the like.

Figure 5:
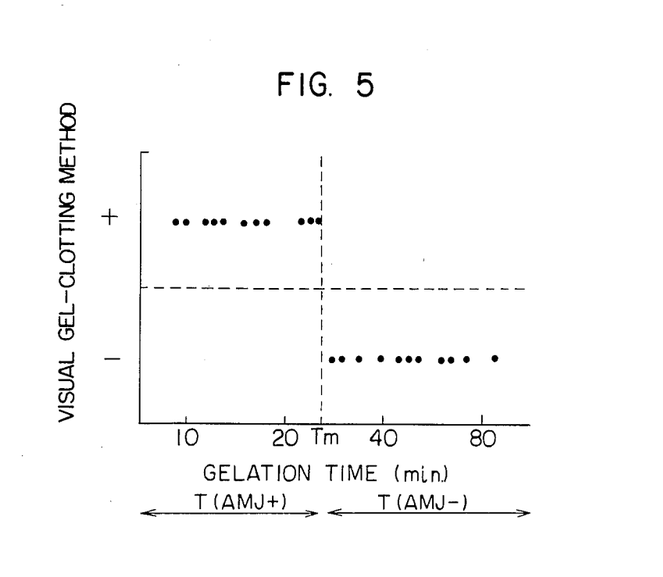
FIG. 5 is a graph showing a relationship between the judgement results according to this invention and those according to a prior art gel-clotting method.

FIG. 5 is a graph showing a comparison between the results of this invention wherein the gelation is judged at $R_{th}$=95% and those of the prior art gel-clotting method, using the same sample solution. The reagent and the measuring method in the process of this invention are the same as used in FIG. 4. As is clear from FIG. 5, the judged results according to the both methods show good agreement. According to the prior art gel-clotting method, only the judgement of two evaluations of positive (+) or negative (−) is given to the sample solution after 60 minutes as to the gelation state. Therefore, this invention can give two evaluation judgement of automatic judgement positive (AMJ+) or automatic judgement negative (AMJ −) in a certain measuring time Tm by the gelation judgement. But, according to the prior art method, the judgement of positive (+) can only be given to sample solutions wherein R(t) reaches Rf, whereas in this invention, the judgement of positive can be given at an earlier stage before R(t) reaches Rf. For example, since Tm is 25 minutes in this invention, it is possible to obtain the same judgement in about half or less measuring time of the prior art method. Further, no skill is necessary at the time of judgement and objective results with no personal difference can be obtained. In addition, when Tm is prolonged, the gelation at a lower concentration of endotoxin which cannot be judged by the prior art method can be detected.

The process of this invention is particularly effective when a plurality of sample solutions are measured by using a plurality of optical systems in parallel. When a plurality of samples are measured by a plurality of optical systems as shown in FIG. 1, since measured I(t) values are quite different in each optical system and each sample, the measurement in parallel is impossible according to prior art methods considering that the values obtained in individual optical systems are equivalent. In contrast, according to the process of this invention, since values of I(t) in individual optical systems are measured with the lapse of time and divided by the individual initial values $I_0$, sensitivity difference depending on each optical system and sensitivity difference due to difference in samples are cancelled. The ratio R(t) is a ratio of transmitted light amounts obtained by correcting properties of individual optical systems by the initial value $I_0$ (that is, a correct initial transmitted light amount obtained by removing variations and noises of the sample solution immediately after the mixing) appeared in the stage (a) before the beginning of gelation shown in FIG. 2. Therefore, the ratio R(t) is an exchangeable amount in each optical system. The gelation point can be judged by providing a proper threshold value $R_{th}$ preferably in the range of 75 to 97% in terms of R(t). The gelation time $T_G$ is derived from the gelation point, which is also determined by the certain value $R_{th}$ which is not dependent on the optical system. Thus, it becomes possible to measure endotoxin concentrations in a plurality of optical systems in parallel by using $T_G$ which is independent from properties of individual optical systems. Further, parallel measurements in individual optical systems make it possible to keep each sample solution still from the beginning of the reaction to the end of the measurement. In addition, the danger of breaking gels by moving sample solutions one after another for measurement as in the prior art methods can be removed.

The present invention wherein a plurality of optical systems measuring changes of transmitted light amounts are treated equally and applied to parallel measurement of endotoxin concentrations is not disclosed in any prior art references.

In this invention, when $R_{th}$ is provided in the range of 75 to 97% in terms of R(t), high precision determination of endotoxin concentration in a by far wider range than any prior art methods becomes possible.

When $R_{th}$ is provided at lower than 75%, for example, $R_{th}$=70%, it becomes very difficult to detect the gelation and no calibration curve is obtained, or if obtained the range of calibration curve is very narrowed to 0.1 to 10 ng/ml. On the other hand, when $R_{th}$ is provided at higher than 97%, the moving (convection) in a sample solution immediately after the mixing of the LAL reagent and the liquid sample, or the variation of R(t) due to the movement of bubbles is possibly judged as gelation by mistake. Therefore, in order to prevent an erroneous detection due to such noises, the range of 3% is necessary for allowance of noise.

That is, $R_{th}$ is provided in the range of 75 to 97%, preferably in the range of 80 to 95%.

The detection sensitivity and the measurable range are different depending on the sensitivity of LAL reagent used. But in any cases, the sensitivity according to this invention is by far higher than that of the gel-clotting method which is one of the prior art methods and the measurable range according to this invention is by far wider than that of the colorimetric method using a synthetic substrate.

Figure 6:
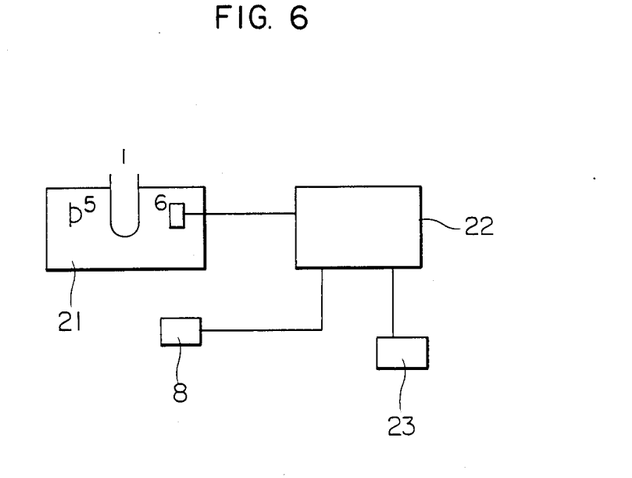
FIG. 6 is a schematic diagram showing fundamental components of an apparatus of this invention.

The apparatus used for the process of this invention fundamentally comprises as shown in FIG. 6, wherein there are one or more optical systems each comprising a light source 5, a sample solution-holding vessel 1 and a means 6 for detecting transmitted light amounts; a constant temperature bath 21 for maintaining the optical systems at a constant temperature and keeping the vessel 1 still; a means 22 for correcting the sensitivity of the optical systems and for judging a gelation point; a means 8 for instructing the initiation of measurement of transmitted light amounts connected to the means 22 for correction and judgement; and a timer 23 for measuring the time passed from the initiation of measurement of transmitted light amounts for each optical system in parallel and independently and connected to the means 22 for correction and judgement.

The means 22 has functions of (a) starting the timer 23 by the initiation of measurement instructed by the measurement initiating means 8, (b) beginning to measure transmitted light amounts, (c) measuring transmitted light amounts with the lapse of time, (d) conducting the correction of the sensitivity of each optical system, e.g. obtaining the ratio $R(t) = I(t)/I_0$, or correction of sensitivity using absorbances which are obtained by measuring transmitted light amounts of a reference and a sample and obtaining their ratio, (e) judging a gelation point, (f) stopping the timer 23 at the time of judging the gelation, etc. These functions can be performed by one device such as a computer, or by two or more devices separately or in combination.

Figure 7:
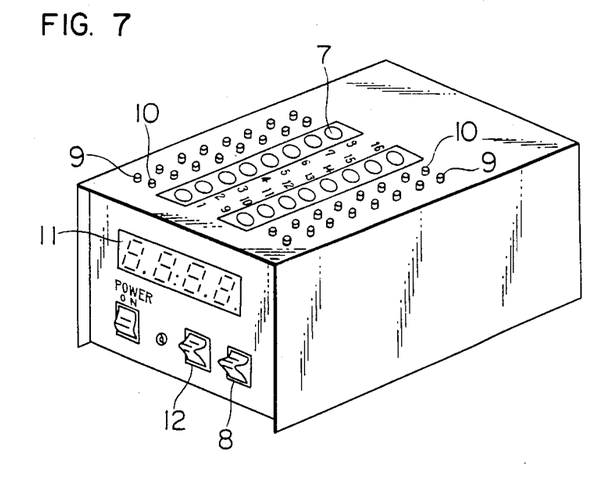
FIG. 7 is a perspective view of outer appearance of one example of the apparatus of this invention.

One concrete example of such an apparatus is shown in FIG. 7. In FIG. 7, a plurality of cuvette holders 7 for holding cuvettes 1 for measurement are provided in one apparatus. Each one optical system for measuring transmitted light amounts is provided in one holder 7. It is also possible to apply a light to each holder by using an optical fiber from one light source. Further, all the holders are kept at a constant temperature such as at 37° C. by a constant temperature bath (not shown in FIG. 7) or a dry temperature controlling apparatus. After fixing each cuvette containing a sample therein in a holder, the sample can be maintained at a still state until the end of the measurement and the measurement can be conducted without giving any moving so as to break the gel state. After fixing a cuvette for measurement containing a mixture of a liquid sample and the LAL reagent in a cuvette holder 7, a switch 8 for instructing the beginning of the measurement is instantly pushed to begin the measurement of the sample.

Then, the switch 8 is pushed every time when a cuvette for measurement is fixed in a holder 7 in a similar manner to conduct the parallel measurement of a plurality of samples with an optional timing within the number of cuvette holders provided in the apparatus. FIG. 7 shows that it is possible to fix 16 cuvettes in the holders in the apparatus. But the number of cuvettes measurable at a time is not limited to such a number of 16 and can be increased or decreased if desired so long as the capacity for control is permissible. It is also possible to connect the switch 8 for instructing the beginning of measurement to each cuvette holder 7. It is further possible to switch every time when a cuvette is fixed.

Figure 9:
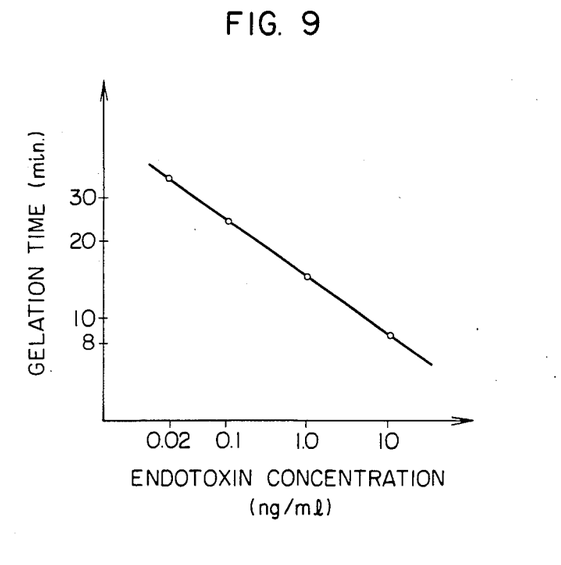
FIG. 9 is a graph showing a calibration curve obtained from the results of Example 1.

It is possible to install a number of measurement display LED (light-emitting diode) 9 for displaying the state of corresponding optical systems. By such displays, it is possible to know which optical system is to be measured from the time of pushing the switch 8 or which optical system is in the course of measurement. Further, when a number of gelation judgement display LED 10 are installed in the apparatus, the judgement of positive/negative for each sample can be displayed. Thus, the same results as obtained by the prior art method of judging by the naked eye can be displayed objectively with high precision in a short time. In addition, when the gelation time $T_G$ based on the gelation judgement of each optical system is displayed by a number of gelation time display LED 11, the determination of endotoxin concentration becomes possible from the relation between the endotoxin concentration and $T_G$ as shown in FIG. 9 rapidly with good reproducibility in addition to the positive/negative judgement.

A display control switch 12 can be used for changing one after another the display of each $T_G$ of each sample when a plurality of samples are measured. It is also possible to display as a whole by using another display method such as CRT display.

Figure 8:
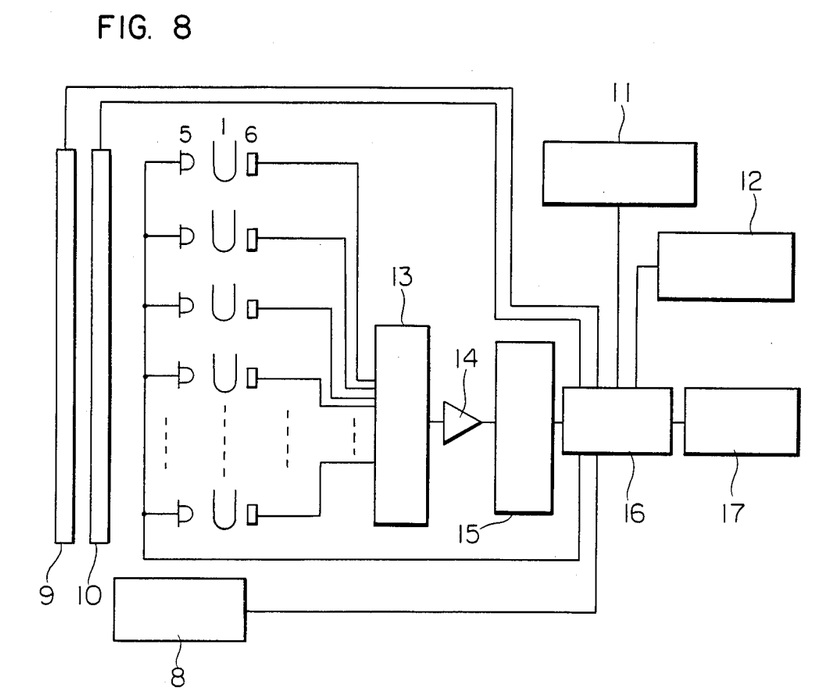
FIG. 8 is a block diagram showing an electric system of one example of the apparatus of this invention.

FIG. 8 is a block diagram showing an electric system of one example of the apparatus of this invention. In FIG. 8, the constant temperature controlling system around the cuvettes for measurement is omitted for simplicity and only the optical measurement controlling system is shown. The transmitted light amounts obtained from a plurality of photoelectric detectors 6 are selected one after another successively by a multiplexer 13, converted to R(t) by a ratio operating circuit 14, and input into an A/D converter 15. The signal converted to digital amount by the A/D converter is processed by a computer 16 to give the judgement of gelation and the determination of $T_G$. The gelation judgement display 10 and the gelation time display LED 11 are also controlled by the computer. It is also possible to print out the measurement results by a printer 17. It is still possible to connect the computer 16 to one or more outer computers, if required, depending on purposes.

According to this invention, it is not necessary to use specially shaped cuvettes for the measurements and there can be used ordinary cuvettes used for a prior art manual method.

As mentioned above, this invention provides an apparatus for measuring endotoxin in a plurality of samples in parallel and effectively with high reliability.

Further according to the process of this invention, the presence of endotoxin in one or more samples can be detected qualitatively with high sensitivity at one time or successively in a short time by measuring the gelation point.

Moreover, according to the process of this invention, the concentration of endotoxin in one or more samples can be determined with high precision and high reliability at one time or successively in a short time by measuring the gelation time $T_G$ from the gelation point.

This invention is illustrated by way of the following Examples.

EXAMPLE 1

Using an apparatus fundamentally similar to that shown in FIGS. 7 and 8 but capable of measuring 64 cuvettes at a time, 10 liquid samples containing endotoxin in a concentration of 0.02 ng/ml were measured in 10 optical systems at one time to determine the gelation time $T_G$.

Reagents and conditions used for the measurement were as follows.

LAL reagent: manufactured by Associates of Cape Cod.

The sensitivity was detected by FDA reference.

Endotoxin: purified from *Escherichia coli* UKT-B (Research Institute for Microbial Diseases, Osaka University). The content was determined by FDA reference.

Measuring conditions: The LAL reagent and the endotoxin were dissolved in distilled water for injection (manufactured by Otsuka Pharmaceutical Co., Ltd.), respectively, and mixed in each test tube having a diameter of 10 mm in amounts of each 0.1 ml with stirring, and changes of transmitted light amounts were measured while maintaining the sample solutions at 37° C.

The results are shown in Table 1.

TABLE 1

| Optical system No. | Initial value $I_{0\text{-}max}$ (mV) | $R(t)$, t = 60 (%) | Gelation time $T_G$ (min) |
|---|---|---|---|
| 1 | 162 | 82.7 | 32.0 |
| 2 | 157 | 83.5 | 35.5 |
| 3 | 269 | 84.7 | 36.0 |
| 4 | 215 | 84.7 | 35.3 |
| 5 | 145 | 84.7 | 35.5 |
| 6 | 141 | 84.3 | 34.8 |
| 7 | 183 | 84.7 | 34.8 |
| 8 | 77 | 82.4 | 32.3 |
| 9 | 120 | 84.3 | 32.5 |
| 10 | 109 | 84.3 | 35.3 |
| $\bar{x}$ | 158 | 84.0 | 34.4 |
| SD | 54.8 | 0.864 | 1.52 |
| CV | 34.8% | 1.03% | 4.41% |

As shown in Table 1, although the initial values ($I_{0\text{-}max}$) which are the transmitted light amounts by themselves are different in respective optical systems, the ratio $R(t)=I(t)/I_{0.max}$ (t=60) shows almost the same values indifferent to the optical systems. In Table 1, the period of 60 minutes from the beginning of the reaction is take as "t" in the ratio $R(t)$. $R_{th}=92\%$ is taken so as to obtain the gelation time $T_G$.

As is clear from the results in Table 1, the judgement of gelation of samples is obtained objectively as in the case of the prior art turbidity measuring method, and in addition a plurality of samples can be judged in parallel with stable high precision using the corresponding number of optical systems effectively.

In the next place, using other 30 optical systems, each 10 samples containing 0.1 ng/ml, 1.0 ng/ml or 10 ng/ml of endotoxin (a total number of 30) were measured at one time in the same manner as described above.

The results are shown in Table 2. As shown in Table 2, properties of individual optical systems are cancelled to give stable values.

TABLE 2

| Endotoxin content (ng/ml) | 0.1 | 1.0 | 10 |
|---|---|---|---|
| Sample number | 10 | 10 | 10 |
| $R(t)$ (t = 60) | | | |
| $\bar{x}$ (%) | 82.0 | 84.7 | 84.2 |
| SD | 1.52 | 0.884 | 1.28 |
| CV (%) | 1.86 | 1.04 | 1.52 |
| Gelation time $T_G$ | | | |
| $\bar{x}$ (min) | 23.5 | 14.3 | 8.25 |

TABLE 2-continued

| Endotoxin content (ng/ml) | 0.1 | 1.0 | 10 |
|---|---|---|---|
| Sample number | 10 | 10 | 10 |
| SD | 1.21 | 0.804 | 0.417 |
| CV (%) | 5.17 | 5.61 | 5.05 |

FIG. 9 shows a calibration curve obtained from the relation between the endotoxin content and the gelation time $T_G$ prepared from the results of Tables 1 and 2.

As mentioned above, according to the process of this invention, the endotoxin contents in a plurality of samples can be measured by using a plurality of optical systems with no personal difference and with good reproducibility. Further, by conducting parallel measurement of the samples, the stable measurement with high efficiency and high reliability becomes possible. Since the apparatus fundamentally the same as shown in FIGS. 7 and 8 but capable of measuring 64 cuvettes at one time is used, data of 40 samples as shown in Tables 1 and 2 were able to be measured within 60 minutes as a total.

EXAMPLE 2

Endotoxin concentrations were measured under the following conditions:

LAL reagent: manufactured by Associates of Cape Cod. The sensitivity according to the gel-clotting method using FDA reference was 0.05 ng/ml.

Endotoxin: purified from *Escherichia coli* UKT-B (Research Institute for Microbial Diseases, Osaka University). The content was determined by FDA reference.

Measuring method: The LAL reagent and the endotoxin were dissolved in distilled water for injection (manufactured by Otsuka Pharmaceutical Co., Ltd.), respectively, and mixed in each test tube having a diameter of 10 mm in amounts of each 0.1 ml with stirring, and changes of transmitted light amounts were measure while maintaining the sample solutions at 37° C.

Figure 10:
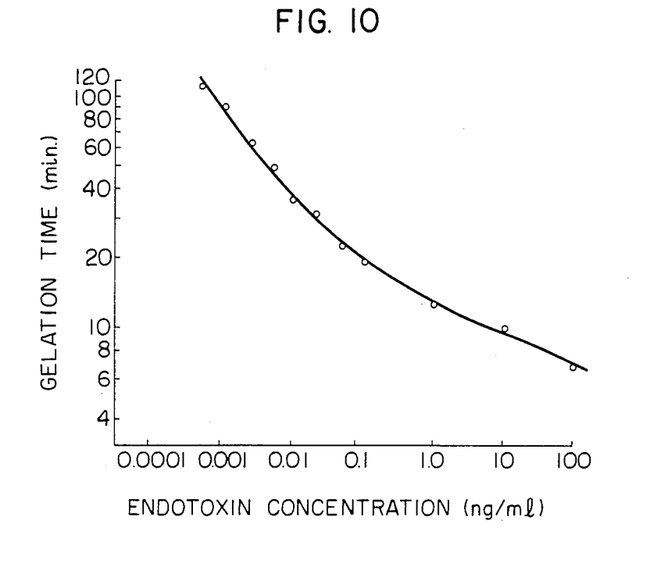
FIGS. 10–12 are graphs showing calibration curves obtained from the results of Examples 2, 4 and 5, respectively.

FIG. 10 shows a calibration relation between the gelation times and the endotoxin concentrations when $R_{th}$ was provided at 95%. As is clear from FIG. 10, the good calibration relationship can be obtained in a very wide range of from 0.0005 ng/ml to 100 ng/ml according to this Example. The sensitivity in this Example is 100 times as high as that obtained by the prior art gel-clotting method using the same reagents. Further, the measurable range according to this Example is a dynamic range of 1000 times or more as wide as that of the colorimetric method using the synthetic substrate.

When $R_{th}$ was provided at 70% in this Example, no gelation was detected and no calibration curve was obtained.

EXAMPLE 3

Six sample solutions containing different endotoxin contents were used for measuring the gelation time under the same measuring conditions as Example 2 within the range of calibration curve obtained in Example 2. The measurement was repeated 16 times as to one kind of sample solution.

The reproducibility of the gelation time $T_G$ and the endotoxin concentration values obtained by using the calibration curve of FIG. 10 is shown in Table 3.

TABLE 3

| Sample No. | 1 | 2 | 3 | 4 | 5 | 6 |
|---|---|---|---|---|---|---|
| Gelation time $T_G$ | | | | | | |
| $\bar{x}$ (min) | 10.4 | 15.9 | 28.0 | 36.6 | 50.7 | 75.2 |
| SD | 0.215 | 0.225 | 0.518 | 0.689 | 1.15 | 3.36 |
| CV (%) | 2.08 | 1.42 | 1.85 | 1.88 | 2.27 | 4.46 |
| Concentration | | | | | | |
| $\bar{x}$ (pg/ml) | 5390 | 346 | 26.1 | 11.8 | 4.25 | 1.54 |
| SD | 761 | 27.4 | 1.51 | 0.663 | 0.269 | 0.175 |
| CV (%) | 14.1 | 7.93 | 5.79 | 5.64 | 6.31 | 11.4 |

As is clear from Table 3, the CV value of $T_G$ is as excellent as below 4.5% and the CV value of the concentration is as excellent as below 15%. Such a high precision determination of endotoxin concentration in a very wide range was impossible according to any prior art methods and becomes possible by the process of this invention. Further the measuring operation of this invention is as simple as the gel-clotting method.

EXAMPLE 4

Figure 11:
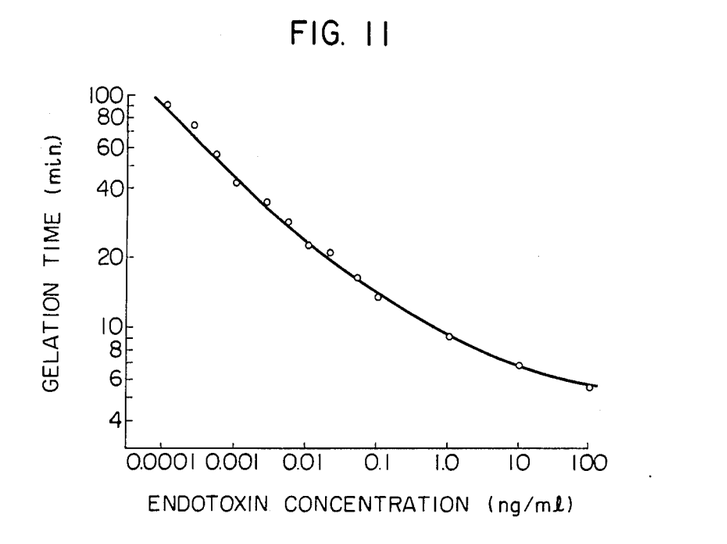

Endotoxin concentrations were measured under the following conditions:
LAL reagent: manufactured by Associates of Cape Cod. The sensitivity according to the gel-clotting method using FDA reference was 0.01 ng/ml.
Endotoxin: the same as Example 2.
Measuring method: the same as Example 2.
FIG. 11 shows a calibration relation between the gelation times and the endotoxin concentrations when $R_{th}$ was provided at 95%. As is clear from FIG. 11, the calibration relation can be obtained in the endotoxin concentrations from 0.0001 to 100 ng/ml. The sensitivity according to this Example is 100 times as high as that obtained by the gel-clotting method using the same reagents. Further, the measurable range according to this Example is a dynamic range of about 10,000 times as wide as that of the colorimetric method using the synthetic substrate.
When $R_{th}$ was provided at 70% in this Example, no gelation was detected and no calibration curve was obtained.

EXAMPLE 5

Figure 12:
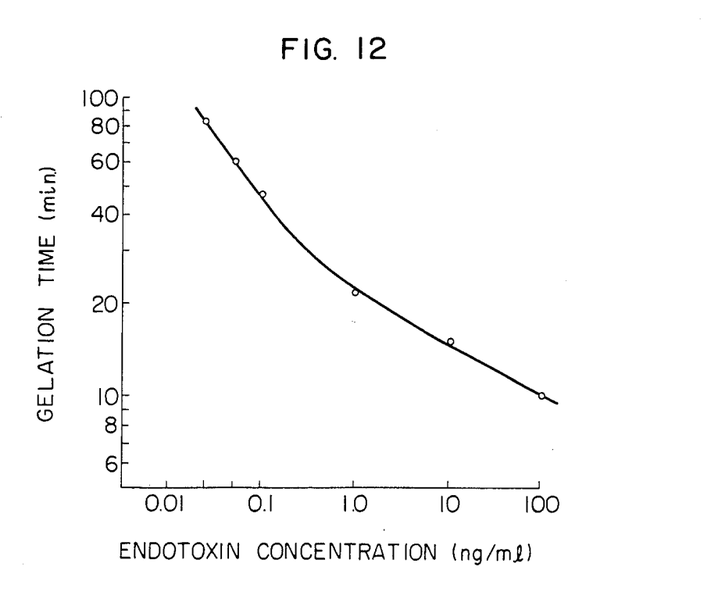

Endotoxin concentrations were measured under the following conditions:
LAL reagent: manufactured by Associates of Cape Cod. The sensitivity according to the gel-clotting method using FDA reference was 0.1 ng/ml.
Endotoxin: the same as Example 2.
Measuring method: The endotoxin was dissolved in distilled water for injection (manufactured by Otsuka Pharmaceutical Co., Ltd.) to give a liquid sample. Freeze-dried LAL reagent and 0.2 ml of the liquid sample were placed in a test tube having a diameter of 12 mm and stirred to dissolve the LAL reagent. Changes of transmitted light amounts were measured while maintaining the sample solution at 37° C.
FIG. 12 shows a calibration relation between the gelation time and the endotoxin concentrations when $R_{th}$ was provided at 85%. As is clear from FIG. 12, the calibration relation can be obtained in the endotoxin concentrations from 0.02 to 100 ng/ml. The sensitivity according to this Example is 5 times as high as that obtained by the gel-clotting method using the same reagents. Further, the measurable range according to this Example is a dynamic range of 50 times as wide as that of the colorimetric method using the synthetic substrate.
When $R_{th}$ was provided at 70% in this Example, the concentration range having the calibration relation was very narrowed to the endotoxin concentration of 0.1 to 10 ng/ml.

What is claimed is:

1. A process for measuring an endotoxin which comprises
    mixing a sample with an endotoxin gelating reagent to give one or more sample solutions,
    applying a light to each sample solution,
    measuring a transmitted light amount at an initial stage $I_0$ and that after a reaction time t, $I(t)$, in each sample solution to give a ratio $R(t)=I(t)/I_0$, and
    judging a gelation point by the ratio R(t) reaching a certain value in the range of 75 to 97%.

2. A process according to claim 1, wherein the initial value $I_0$ is a maximum initial value $I_{0.max}$, an average initial value $I_{0.av}$, a minimum initial value $I_{0.min}$, or an initial value at a special point of time "ts" $I_{0.ts}$.

3. A process according to claim 1, which further comprises
    obtaining a gelation time $T_G$ from a time required for reaching the gelation point from the mixing of the sample and the endotoxin gelating reagent, and
    determining the endotoxin content in the sample.

4. A process according to claim 3, wherein two or more sample solutions are used in parallel.

5. A process according to claim 3, wherein the initial value $I_0$ is a maximum initial value $I_{0.max}$, an average initial value $I_{0.av}$, a minimum initial value $I_{0.min}$, or an initial value at a special point of time "ts", $I_{0.ts}$.

6. An apparatus for measuring an endotoxin comprising
    one or more optical systems each comprising a light source, a sample solution-holding vessel, and a means for detecting transmitted light amounts,
    a constant temperature bath for maintaining the optical systems at a constant temperature and keeping the vessel still,
    a means for correcting the sensitivity of the optical systems and for judging a gelation point by the ratio $R(t)=I(t)/I_0$, wherein $I_0$ is a transmitted light amount at an initial stage and $I(t)$ is a transmitted light amount after a reaction time t, reaching a certain value in the range of 75 to 97%,
    a means for instructing the initiation of measurement of transmitted light amounts connected to the means for correction and judgment, and
    a timer for measuring the time passed from the initiation of measurement of transmitted light amounts for each optical system in parallel and independently and connected to the means for correction and judgement.

7. An apparatus according to claim 6, wherein the sample solution-holding vessel is a cuvette having an inner diameter of 6 to 12 mm.

8. An apparatus according to claim 6, wherein the means for instructing the initiation of measurement is a switch which can give the instruction to two or more sample solution-holding vessels independently.

9. An apparatus according to claim 6, wherein the means for correcting the sensitivity of the optical systems and for judging a gelation point comprises one or more devices having functions of (a) starting the timer by the initiation of measurement instructed by the means for instructing the initiation of measurement,
(b) beginning to measure transmitted light amounts,
(c) measuring transmitted light amounts with the lapse of time,
(d) conducting the correction of the sensitivity of each optical system,
(e) judging a gelation point, and
(f) stopping the timer at the time of judging the gelation.

10. An apparatus according to claim 6, wherein the means for correcting the sensitivity of the optical systems and for judging a gelation point has a means for transferring data of transmitted light amounts or data of measured time to one or more outer computers.

11. An apparatus according to claim 6, which further comprises at least one device connected to the means for correcting the sensitivity of the optical systems and for judging a gelation point and selected from the group consisting of a measuring state display, a gelation judgement display, a gelation time display and a measuring time display.

12. An apparatus according to claim 11, which further comprises a printer connected to the means for correcting the sensitivity of the optical systems and for judging a gelation point.

13. A process for measuring an endotoxin which comprises
mixing a sample with an endotoxin gelating reagent to give two or more sample solutions,
applying a light to each sample solution,
measuring a transmitted light amount at an initial stage $I_0$ and that after a reaction time t, $I(t)$, in each sample solution to give a ratio $R(t)=I(t)/I_0$, and
judging a gelation point by the ratio R(t) reaching a certain value,
obtaining a gelation time $T_G$ from a time required for reaching the gelation point from the mixing of the sample and the endotoxin gelating reagent, and
determining the endotoxin contents in the samples in parallel.

14. A process according to claim 13, wherein the certain value of R(t) for judging the gelation point is in the range of 75 to 97%.

15. A process according to claim 13, wherein the sample is a liquid sample in an amount of 0.1 ml and the endotoxin gelating reagent is a Limulus amoebocyte lysate reagent in an amount of 0.1 ml.

16. A process according to claim 13, wherein the sample is a liquid sample in an amount of 0.2 ml and the endotoxin gelating reagent is a freeze-dried Limulus amoebocyte lysate reagent.

17. A process according to claim 13, wherein the transmitted light amount at an initial stage $I_0$ is a maximum initial value $I_{0.max}$.

18. A process according to claim 13, wherein the transmitted light amount at an initial stage $I_0$ is an average initial value $I_{0.av}$.

19. A process according to claim 13, wherein the transmitted light amount at an initial stage $I_0$ is a minimum initial value $I_{0.min}$.

20. A process according to claim 13, wherein the transmitted light amount at an initial stage $I_0$ is an initial value at a special point of time "ts", $I_{0.ts}$.

21. An apparatus for measuring an endotoxin comprising
a plurality of optical systems each comprising a light source, a sample solution-holding vessel, and a means for detecting transmitted light amounts, and conducting the measurement of a plurality of samples in parallel,
a constant temperature bath for maintaining the optical systems at a constant temperature and keeping the vessel still,
a means for correcting the sensitivity of the optical systems and for judging a gelation point,
a means for instructing the initiation of measurement of transmitted light amounts connected to the means for correction and judgement, and
a timer for measuring the time passed from the initiation of measurement of transmitted light amounts for each optical system in parallel and independently and connected to the means for correction and judgment.

* * * * *